United States Patent [19]

Schmitt et al.

[11] Patent Number: 5,697,969
[45] Date of Patent: Dec. 16, 1997

[54] VASCULAR PROSTHESIS AND METHOD OF IMPLANTING

[75] Inventors: Peter J. Schmitt, Garnerville, N.Y.; David Stuart Brookstein, Wellesley; John Skelton, Sharon, both of Mass.

[73] Assignee: Meadox Medicals, Inc., Oakland, N.J.

[21] Appl. No.: 530,538

[22] Filed: Sep. 20, 1995

Related U.S. Application Data

[63] Continuation of Ser. No. 119,191, filed as PCT/GB92/00538, Mar. 24, 1992 published as WO92/16166, Oct. 1, 1992, Pat. No. 5,466,257.

[30] Foreign Application Priority Data

Mar. 25, 1991 [GB] United Kingdom ............... 9106347
Mar. 23, 1992 [GB] United Kingdom ............... 9206282

[51] Int. Cl.$^6$ ............... A61F 2/06; A61F 2/04
[52] U.S. Cl. ............... 623/1; 623/13; 623/12; 600/36
[58] Field of Search ............... 606/152–158; 600/36; 623/1, 11, 12, 13

[56] References Cited

U.S. PATENT DOCUMENTS

| | | |
|---|---|---|
| 161,272 | 3/1875 | Reed . |
| 200,965 | 3/1878 | Baker . |
| 299,017 | 5/1884 | Schenck et al. . |
| 299,018 | 5/1884 | Schenck et al. . |
| 348,698 | 9/1886 | Sibley . |
| 427,929 | 5/1890 | Stowe . |
| 456,620 | 11/1891 | Stowe . |
| 532,902 | 1/1895 | Palmer . |
| 610,463 | 9/1898 | Stowe . |
| 697,390 | 4/1902 | Beck . |
| 697,391 | 4/1902 | Beck et al. . |
| 697,392 | 4/1902 | Beck et al. . |
| 899,092 | 9/1908 | Alvord . |
| 1,164,304 | 12/1915 | Nicewarner . |
| 2,025,039 | 12/1935 | Cannon . |
| 2,978,787 | 4/1961 | Liebig . |
| 3,000,076 | 9/1961 | Runton et al. . |
| 3,095,017 | 6/1963 | Bleiler et al. . |
| 3,105,492 | 10/1963 | Jeckel . |
| 3,272,204 | 9/1966 | Artandi et al. . |
| 3,316,557 | 5/1967 | Liebig . |
| 3,317,924 | 5/1967 | LeVeen et al. . |
| 4,025,684 | 5/1977 | Neidhardt . |
| 4,086,941 | 5/1978 | Thompson . |
| 4,193,137 | 3/1980 | Heck . |
| 4,312,261 | 1/1982 | Florentine . |
| 4,346,741 | 8/1982 | Banos et al. . |
| 4,416,028 | 11/1983 | Eriksson et al. ............ 623/1 |
| 4,441,215 | 4/1984 | Kaster . |
| 4,670,286 | 6/1987 | Nylies et al. . |
| 4,719,837 | 1/1988 | McConnell et al. . |
| 4,728,329 | 3/1988 | Mansat . |

(List continued on next page.)

FOREIGN PATENT DOCUMENTS

| | | |
|---|---|---|
| 0 117 072 A1 | 8/1984 | European Pat. Off. . |
| 0 317 408 | 3/1989 | European Pat. Off. . |
| 2583072 A1 | 12/1986 | France . |
| 8705796 | 10/1987 | WIPO ............ 623/1 |
| WO 88/00813 | 2/1988 | WIPO . |
| WO 90/12550 | 11/1990 | WIPO . |

OTHER PUBLICATIONS

R.T. Brown, "Three-Dimensional Braiding", *Handbook of Industrial Braiding* (undated).
Atkins Pearce, *Formation of Industrial Braids*, pp. 3.1–3.12 (undated).

*Primary Examiner*—Debra S. Brittingham
*Attorney, Agent, or Firm*—Hoffmann & Baron LLP

[57] ABSTRACT

The present invention provides a vascular prosthesis which comprises a braided tubular fabric comprising a plurality of braid layers wherein each layer includes at least one interlocking yarn which extends from that layer into another layer to form an interlock therewith. In one aspect of the invention, the plurality of braid layers may include a substantially non-absorbable first surface layer and a substantially resorbable second surface layer.

15 Claims, 13 Drawing Sheets

U.S. PATENT DOCUMENTS

| | | |
|---|---|---|
| 4,743,250 | 5/1988 | Kitagawa et al. . |
| 4,834,747 | 5/1989 | Gogolewski . |
| 4,834,755 | 5/1989 | Silvestrini et al. . |
| 4,917,699 | 4/1990 | Chervitz ................................. 623/13 |
| 4,917,700 | 4/1990 | Aikins . |
| 4,923,470 | 5/1990 | Dumican . |
| 4,975,262 | 12/1990 | Suto et al. . |
| 5,084,065 | 1/1992 | Weldon et al. . |
| 5,091,246 | 2/1992 | Yasui et al. . |
| 5,116,360 | 5/1992 | Pinchuk et al. . |
| 5,357,839 | 10/1994 | Brookstein et al. . |
| 5,376,118 | 12/1994 | Kaplan et al. ............................ 623/13 |

EFFECT OF RELATIVELY LOW RADIAL COMPLIANCE DURING SYSTOLE

OUTER SURFACE

OUTER SURFACE

INNER SURFACE

INNER SURFACE FIG. 8A
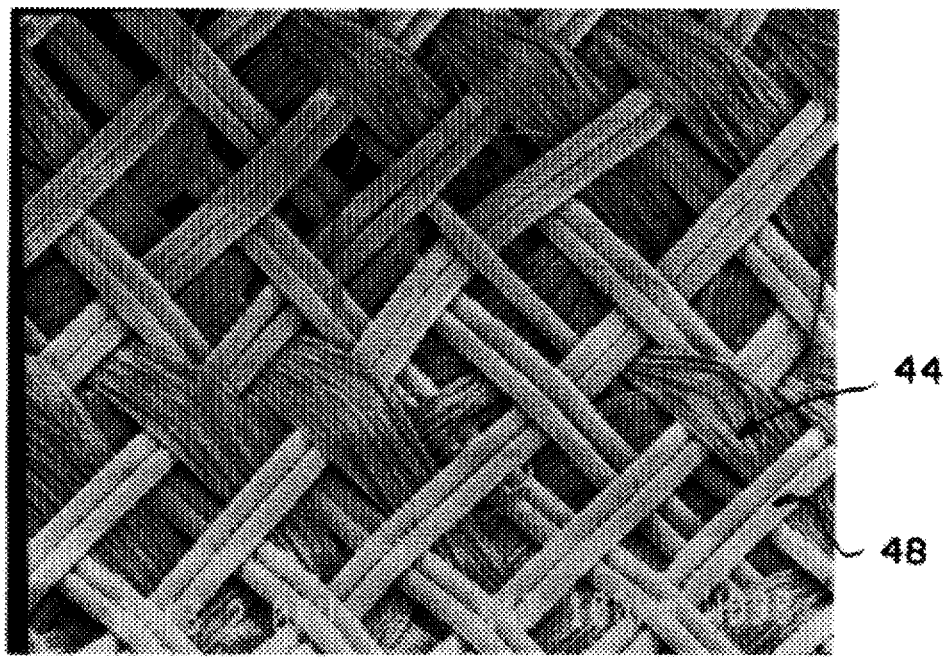
FIG. 8B
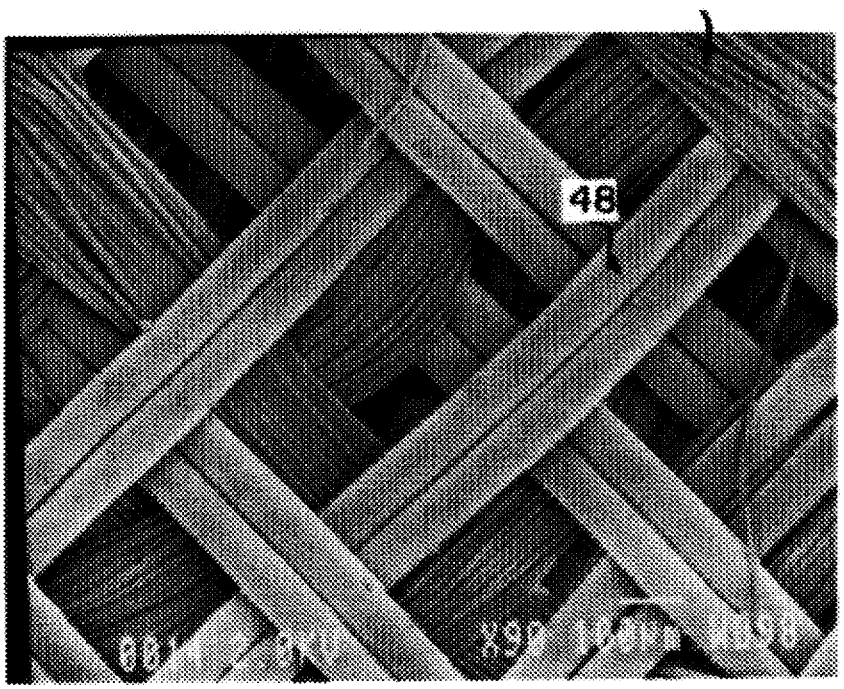

CROSS SECTION

CROSS SECTION FIG. 10A
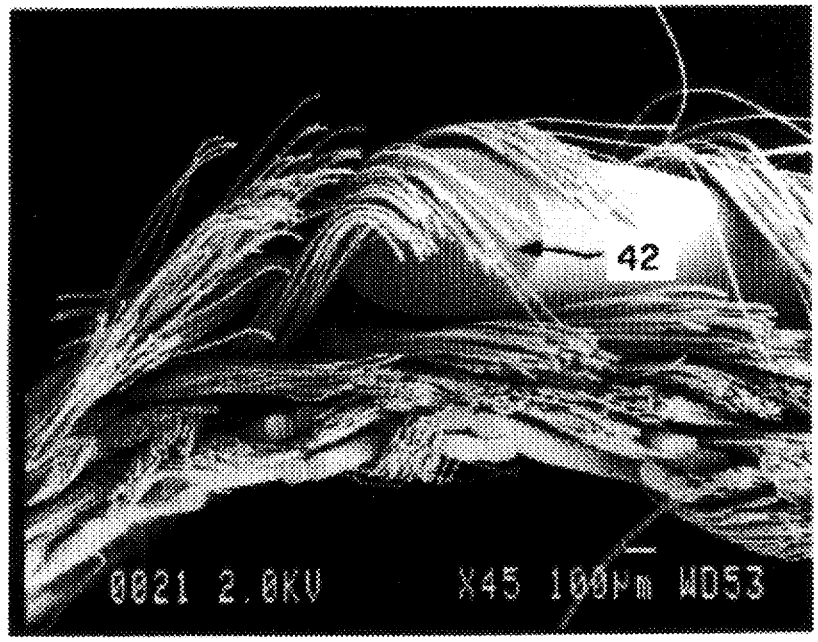
FIG. 10B
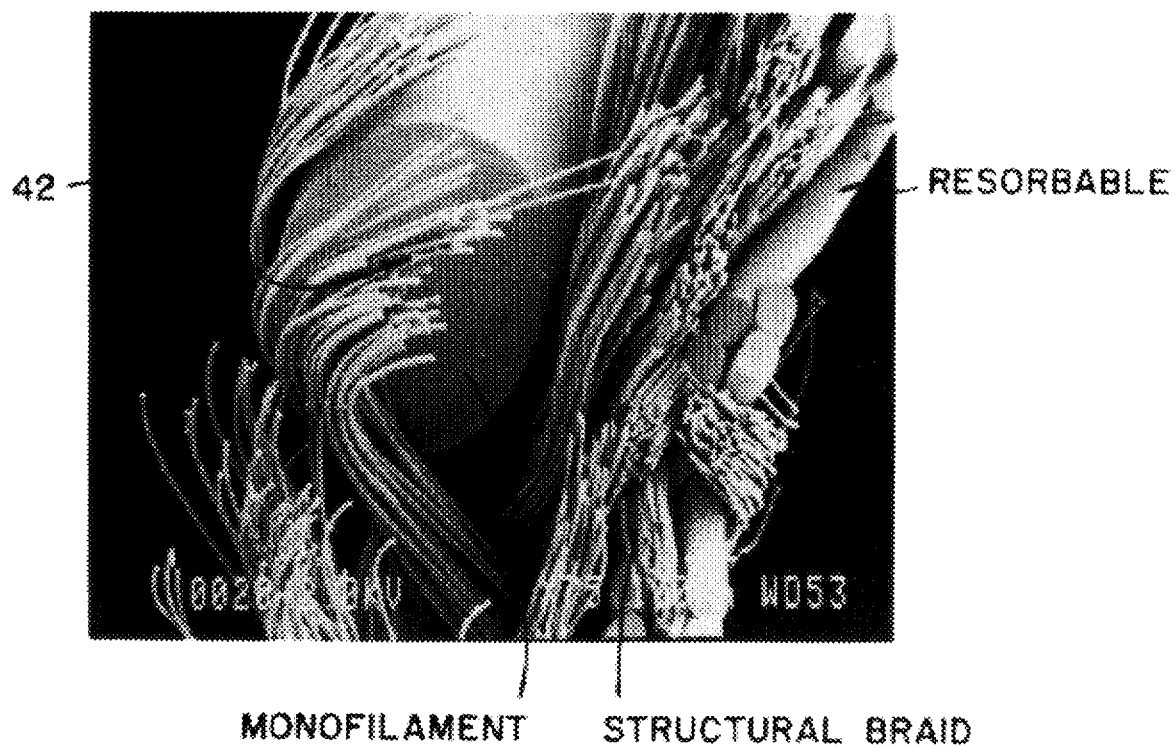

EXTERIOR SURFACE

INTERIOR SURFACE

EXTERIOR SURFACE       INTERIOR SURFACE 6.1

6.2

6.3

6.4

VASCULAR PROSTHESIS AND METHOD OF IMPLANTING

This is a continuation of application Ser. No. 08/119,191, filed as PCT/GB92/00538, Mar. 24, 1992 published as WO92/16166, Oct. 1, 1992, now U.S. Pat. No. 5,466,257.

The present invention relates to a vascular prosthesis.

In surgery, tubular vascular prostheses are typically used for the replacement of damaged or worn-out blood vessels. Such a prosthesis should desirably have properties of radial and longitudinal elasticity which resemble closely the corresponding properties of natural blood vessels, thereby to avoid aneurysm at the anastomosis and to maintain patency of the implant. Further, it is desirable that a synthetic vascular prothesis should allow tissue ingrowth to form a smooth, non-thrombotic endothelium of natural cellular tissue. It will be appreciated, therefore, that after implantation the prosthesis should provide a porous support structure which gives the implant an intrinsic strength matching the strength of a natural blood vessel and allows cellular growth to invade the prosthesis to form a neointimal vessel lining having an organised cell structure. However, immediately on implantation the prosthesis is desirably impermeable to blood, thereby to avoid bleeding without the requirement for preclotting which hinders tissue ingrowth and promotes thrombosis.

A typical tubular vascular prosthesis comprises a tubular fabric which includes a resorbable yarn component, and a non-absorbable yarn component. The yarns are incorporated in the fabric to form a prosthesis which is initially impermeable to blood and, over a period of time following implantation, the biologically absorbable fibres are resorbed, thereby increasing progressively the porosity of the prosthesis to allow ingrowth.

Hitherto, synthetic vascular prostheses have been made by weaving, braiding, knitting or crochetting, but tubular vascular prostheses made of synthetic fibre yarns by weaving or knitting are not suitable for use when the dieter of the prosthesis is less than about 6 mm. Problems such as kinking and anastomotic hyperplasia at the interface between a natural artery or vein and such a tubular prosthesis prevent the use of such a graft having an internal diameter of less than 6 mm.

European Patent Specification NO. A0397500 discloses a vascular prosthesis which is formed by weaving, knitting or braiding a synthetic semi-absorbable composite yarn to form a tubular fabric. The composite yarn comprises a non-absorbable elastic core which imparts resiliency to the composite yarn and an absorbable, relatively inelastic sheath which imparts transverse tensile strength to the composite yarn. In use, the sheath material is progressively resorbed, whereby a porous structure develops which provides a scaffold for tissue ingrowth and exhibits structural properties resembling the dynamic fluid pressure response characteristics of natural vascular tissue. The vascular prosthesis of EP-A-0397500 has an initial low permeability to prevent blood leakage in pre-heparinized patients without the requirement for pre-clotting and an increasing permeability in use to allow the progressive development of a smooth, non-thrombogenic neointima. However, the intrinsic structural characteristics of the prosthesis change as the sheath material is eroded. The graft, therefore, is not satisfactory unless the erosion of the sheath is matched by tissue ingrowth to maintain the strength of the prosthesis.

According to one aspect of the present invention there is provided a vascular prosthesis which comprises a braided tubular fabric comprising a plurality of braid layers wherein each layer includes at least one interlocking yarn which extends from that layer into another layer to form an interlock therewith.

In another aspect of the present invention, the plurality of braid layers may comprise a substantially non-absorbable first surface layer and a substantially resorbable second surface layer.

The braided tubular fabric may be formed by interbraiding one yarn of a non-resorbable material with another yarn of a biologically resorbable material. The first surface layer may be formed substantially only of said one yarn, and the second surface layer may be formed substantially only of said other yarn. Typically, the resorbable material may be selected from catgut (collagen sutures derived from sheep intestinal submucosa), reconstituted collagen, polyglycolic acid (PGA) and its lactide copolymers, polydioxanone (PDS) and poly(glycolide-trimethylene carbonate). The non-absorbable material may be selected from natural fibres such, for example, as silk and cotton and synthetic fibres such, for example, as polyethylene, polypropylene, polyamide, polyester, polytetrafluoroethylene and stainless steel.

According to one aspect the outer surface layer of the fabric is substantially non-absorbable, and the inner or luminal surface layer is substantially resorbable. The fabric my also comprise one or more intermediate layers between said surface layers. Each intermediate layer may be formed of said two yarns interbraided with one another. The proportion of said one yarn in each layer may decrease progressively, and the proportion of said other yarn in each layer may increase progressively from one of said surface layers to the other surface layer.

According to a particular aspect of the invention, the diameter of the tubular braided prosthesis may be about 6 mm or less; although the invention also comprehends prostheses having diameters greater than 6 mm.

In some embodiments, the tubular fabric may include non-absorbable, external support means. The said support means may comprise at least one wrap which follows a helical or spiral path around the exterior of the fabric; and in one aspect the support means includes two wraps, each wrap following a spiral path of opposite handedness to the other wrap.

Each wrap may be formed of an elongate textile structure having a suitably high bending modulus or stiffness. According to some embodiments, each wrap comprises a monofilament or yarn having a high denier. Alternatively, the wrap may be a multifilament yarn or braid formed of a plurality of strands having a high composite denier and a linear density greater than that of the braided tubular fabric.

The wrap may be attached to the external surface of the fabric by any suitable adhesive or by heating to form fibre-to-fibre bonds. Preferably, however, each wrap is incorporated into one or more of the intermediate or external surface layers of the braid forming the fabric. In a particular aspect of the invention, the wrap may be incorporated in the braid structure of the said external surface layer to follow a helical path; more particularly, the said wrap may be incorporated in the braided external suffice layer such that it does not form an interlock with any of the other braid layers. The wrap(s) my be formed of any suitable non-absorbable material; in one embodiment, a polyester wrap may be utilized.

A suitable method and apparatus for forming a tubular braided fabric for use as a vascular prosthesis in accordance with the present invention is disclosed in the specification as published under International Patent Publication No. WO91/10766, the disclosure of which is incorporated herein by reference. According to this method, a braided fabric comprising a plurality of interlocked layers is produced by a plurality of package carriers of yarn which are constrained by track module means to move along a plurality of serpentine paths; the track module means being arranged to extend in a first direction to define a longitudinally extending path corresponding to a first layer of the braided fabric and in a second direction to provide at least one cross-over path between adjacent serpentine paths. The package carriers are moved in said first direction to create a first layer of braid and along a cross-over path between adjacent serpentine paths to cause the yarn forming said first layer of braid to be transported to interlock with the braid of an adjacent layer.

The apparatus for the production of such a braided fabric comprises: a two-dimensional array of rotatable horn gears in toothed engagement; driving means for driving said array, each horn gear being arranged to rotate in a direction contrary to each interengaging gear; track means overlaying said array; and a plurality of yarn package carriers movable along said track means by said horn gears. The track means comprises a plurality of track modules which together define a plurality of serpentine paths extending in a first direction, each serpentine path corresponding to a braid layer in said fabric and in which selected track modules include at least one cross-over path section extending in a second direction between one serpentine path and the next adjacent serpentine path to cause or allow the package carriers to move between adjacent serpentine paths to effect interbraiding of yarns between adjacent layers.

A base bed may be provided on which a plurality of gear modules may be arranged in an infinite array, and over which the track modules may be positioned. The base bed may be disposed in a cylinder and provides a tubular multilayer tubular braid in which the layers are interlocked or interbraided one with another.

A multi-layer braided tubular prosthesis according to the present invention may have the advantage that the structural characteristics of the fabric do not change as the resorbable material is absorbed. In use, therefore, the change in permeability of the fabric as the resorbable material is eroded may coincide with the development of a neointimal surface. Furthermore, it has been found that the use of an interlocked, multi-layer tubular braid of the type disclosed in WO91/10766 permits the production of a prosthesis having a diameter of about 6 mm or less which exhibits an increased resistance to kinking as compared with known prostheses. A small diameter implant in accordance with the present invention may have particular application as a prosthetic graft e.g. for the aorto-coronary artery or the femoral-popliteal artery.

A tubular braided fabric having interlocked layers produced by the method and apparatus of WO91/10766 may be stronger than a conventional tubular braided structure having layers which are not inter-connected. The properties of such a prosthesis tend to degrade over time, and the improved initial strength assists materially the longevity of the prosthesis. The braid prosthesis of the present invention, therefore, may be less vulnerable to kinking when bent. The relatively high radial compression resistance may minimise the effects of anastomotic hyperplasia, and the relatively low radial compliance in tension may accommodate the systolic pressure pulse.

A significant advantage of the vascular prosthesis in accordance with the present invention is that with the braided fabric the lay of the bulk of the yarns constituting the braid is at a significant angle to the longitudinal axis of the prosthesis. In the prior art methods using woven fabrics, one of the yarns of weave usually extends in the longitudinal direction. This means that in use, bending and flexing of such woven prostheses results in much greater stress and strain on such longitudinal yarns thus resulting in kinking and sometimes premature failure of the prosthesis. The angular disposition of the yarns of the prosthesis of the present invention permits of sharp bends in the prosthesis without imparting such strain on the yarns forming the braid.

Following is a description byway of example only and with reference to the accompanying drawings of methods of carrying the present invention into effect.

In the drawings:

FIG. 8 is two photomicrographs at X43 and X90 magnification respectively of the inner surface of the prosthesis of FIG. 4.

FIG. 10 is two photomicrographs at X45 and X75 magnification respectively of the cross-section of FIG. 9.

EXAMPLE 1

Figure 1:
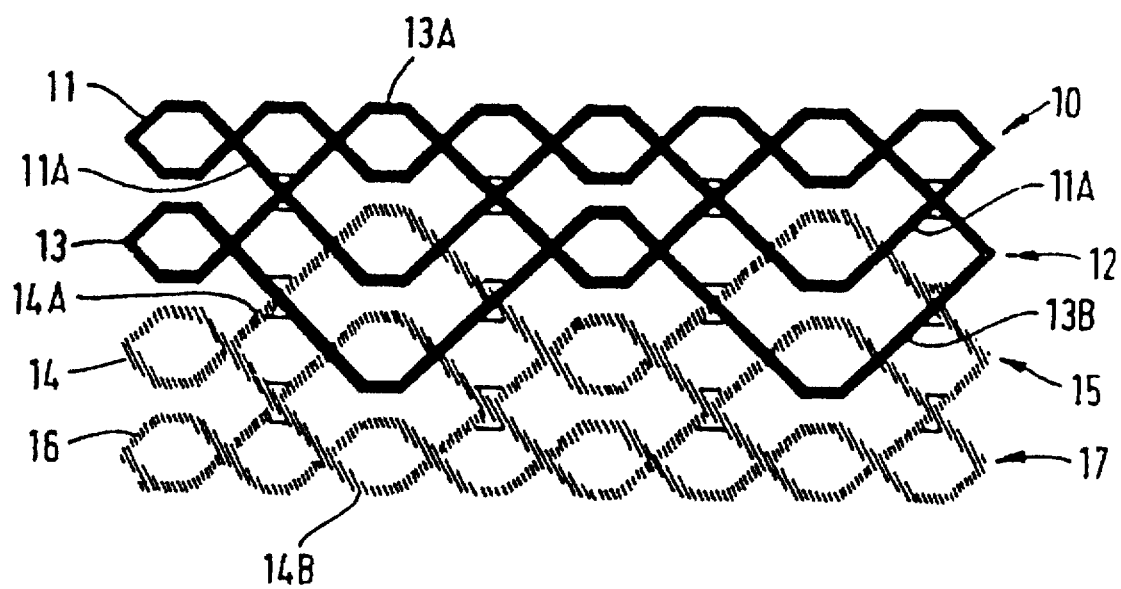
FIG. 1 is a schematic illustration of a cross-section of a fragment of a multi-layer braided fabric tubular prosthesis in accordance with the present invention.

In FIG. 1 a fragment of a multilayer braided fabric tubular vascular prosthesis comprises four inter-locked layers (10), (12), (15) and (17). Each layer is formed by interbraiding two lengths of yarn which follow generally serpentine paths, one path superimposed on and out of phase by half a cycle with respect to the other path. Part of one of the lengths of yarn of each layer is diverted from its serpentine path to extend across to a second layer to be interbraided with one of the yarns forming that second layer; whereafter the one length of yarn is returned to its serpentine path in the first layer. In being interbraided with the yarn of the second layer, the length of yarn is passed around the yarn of the second layer so that the two layers are interlocked. In each layer the diverted portion of the one length of yarn is replaced by a similar diverted portion of yarn diverted from another layer which is interbraided with the first mentioned yarn for interlocking.

The layer (10) that forms the outer surface layer of the tubular prosthesis is formed by non-resorbable yarn material only; pans (11A) of the main length (11) of that material being diverted to interlock with one of the yarns that forms juxtaposed layer (12). In addition to the diverted portions (11A) of the yarn material (11), said juxtaposed layer (12) is formed of portions of each of other lengths (13) and (14) of yarn; length (13) also being formed of non-resorbable material, while the length (14) is formed of resorbable material.

Next juxtaposed layer (15) is formed of portions of three different yarns: yarn (14), diverted portions (13B) of the length of non-resorbable yarn (13) and diverted portions of a length of resorbable yarn (16) which forms inner surface layer (17). Inner layer (17) is also formed of diverted portions (14B) of yarn (14) which are interbraided with yarn (16).

Figure 2:
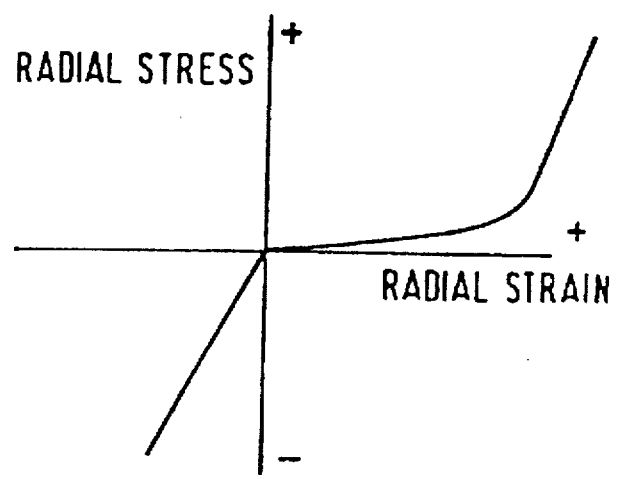
FIG. 2 is a graph of the radial stress strain relationship of the multi-layer braided tubular fabric of FIG. 1.

With reference to FIG. 2 the stress/strain relationship of the tubular prosthesis of Example 1 has a relatively high radial compression resistance and a low radial compliance in tension which minimises the tendency for the prosthesis to kink and reduces the possibility of aneurysm at the anastomosis.

EXAMPLE 2

Figure 3:
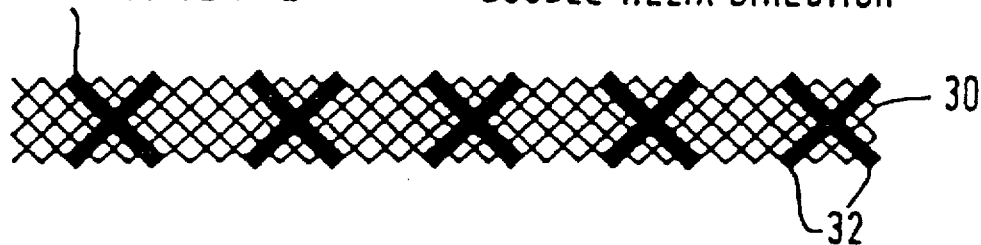
FIG. 3 is a schematic illustration of a braided prosthesis according to the present invention including exterior helical support means.

With reference to FIG. 3, a 5-layer interbraided tubular prosthesis (30) was made on a 6 mm diameter steel mandrel using a 48-carrier braiding machine. The inner braid layer (not shown) was formed substantially of 48 yarns of resorbable 7/0 monofilament suture yarn which is commerically available from Messrs Davis & Geck under the Trade Mark MAXON: the outer braid layer was formed substantially of 46 polyester multifilament yarns of 70 denier of the type commerically available under the Trade Mark "DACRON" type 56 and 2 polyester monofilaments (32) of 0.012" dieter: and the three intermediate layers were each formed substantially of 48 yarns of 70 denier DACRON type 56.

The said polyester monofilaments (32) were incorporated into the braid structure of the outer layer to form two helical wraps in the outer surface of the prosthesis (30); the wraps being of opposite handedness one from the other. After braiding, the prosthesis was removed from the mandrel and placed over a 5 mm diameter mandrel and heat-set at 150° C. for 30 minutes.

EXAMPLE 3

Figure 4:
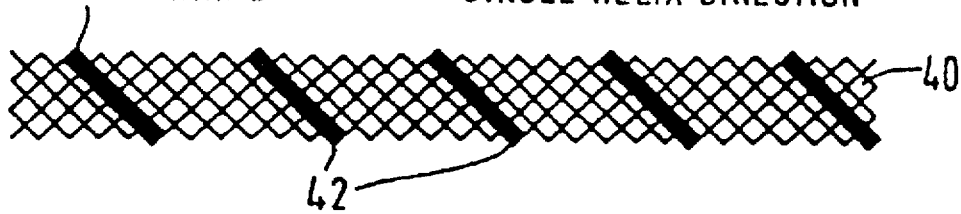
FIG. 4 is a schematic illustration of a different supported tubular braided prosthesis in accordance with the present invention.

In FIG. 4, a tubular vascular prosthesis (40) was made in the same way as described in Example 2 above, but the outer braid layer was formed with only one helical wrap (42) of polyester monofilament.

Figure 6A:
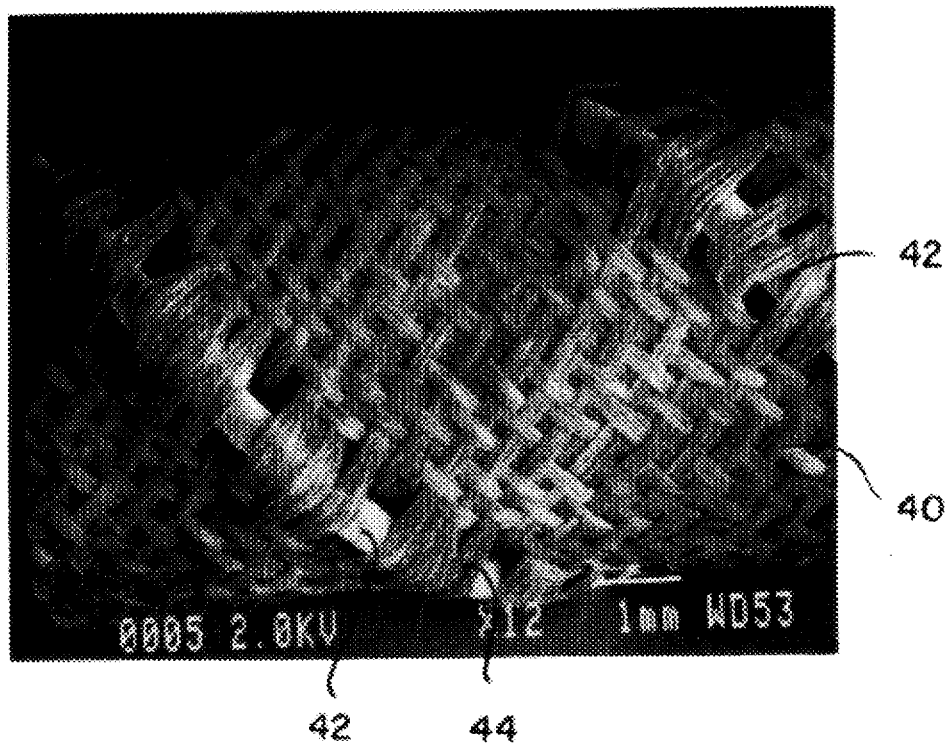
FIG. 6 is two photomicrographs at X12 magnification of the prosthesis of FIG. 4.
Figure 6B:
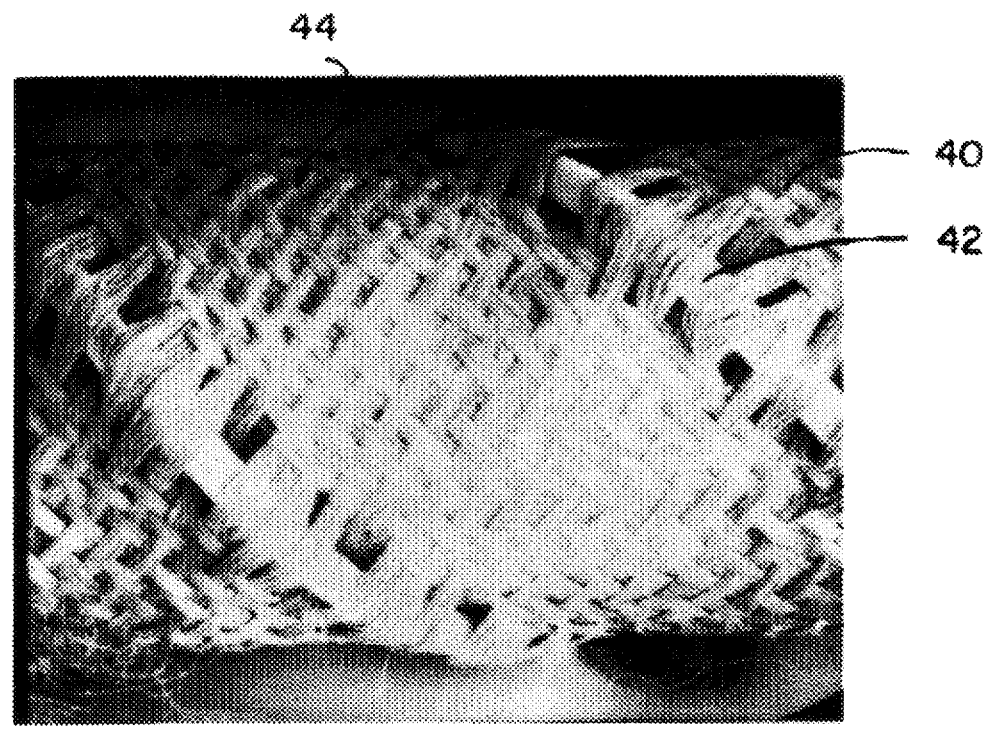
Figure 7A:
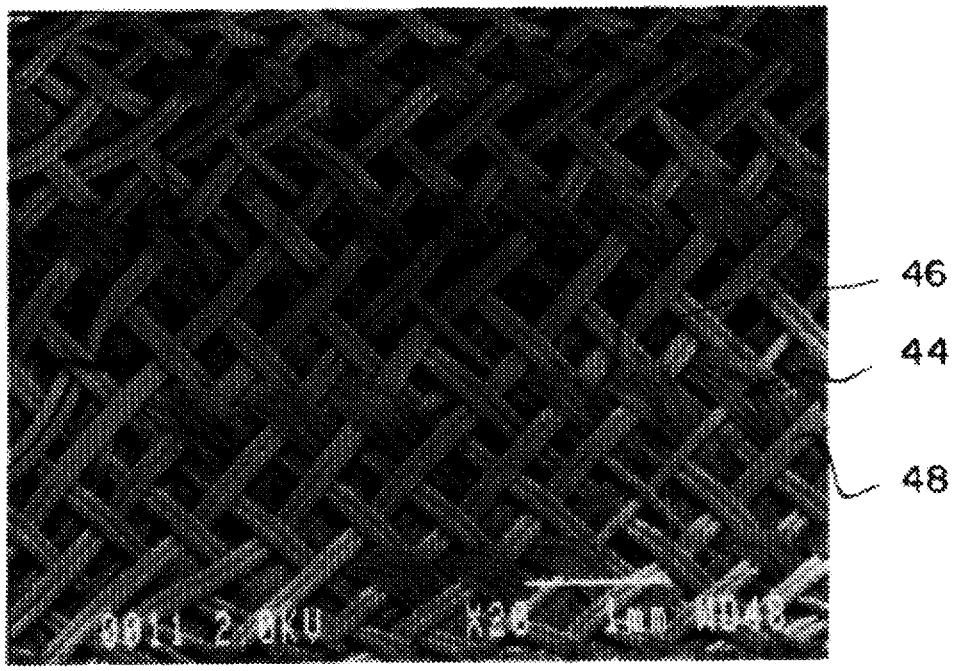
FIG. 7 is two photomicrographs at X20 and X25 magnification respectively of the inner surface of the prosthesis of FIG. 4.
Figure 7B:
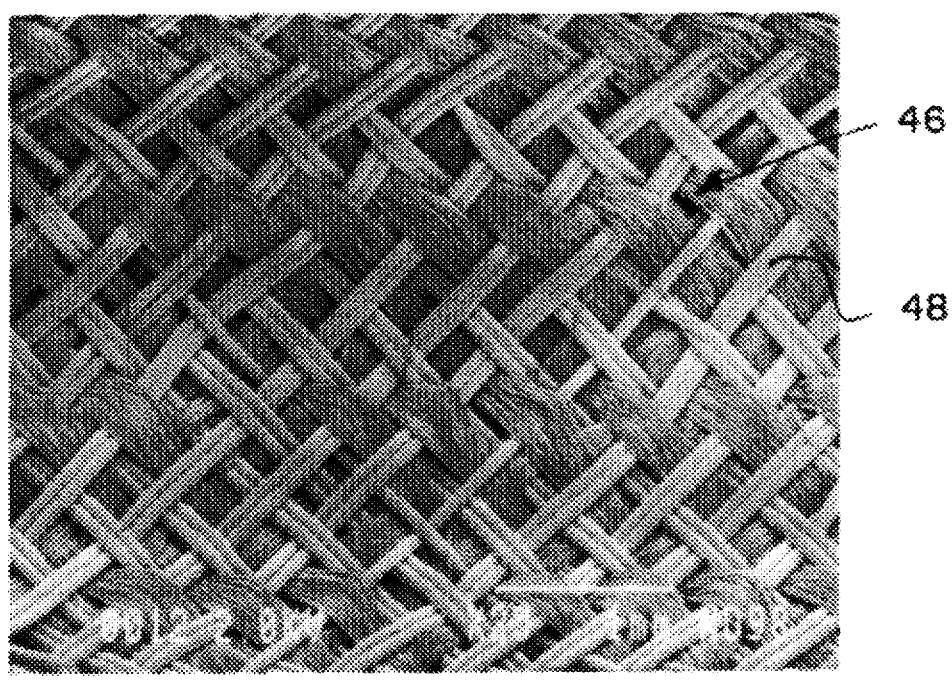
Figure 9A:
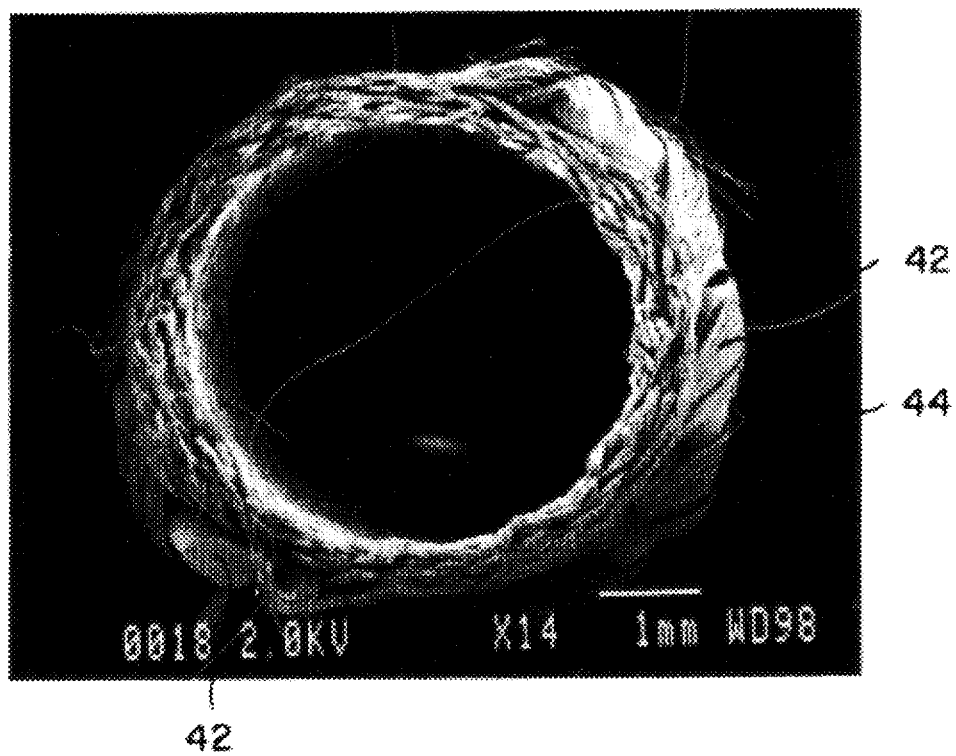
FIG. 9 is two photomicrographs at X14 and X33 magnification respectively which show a cross-sectional view of the prosthesis of FIG. 4.
Figure 9B:
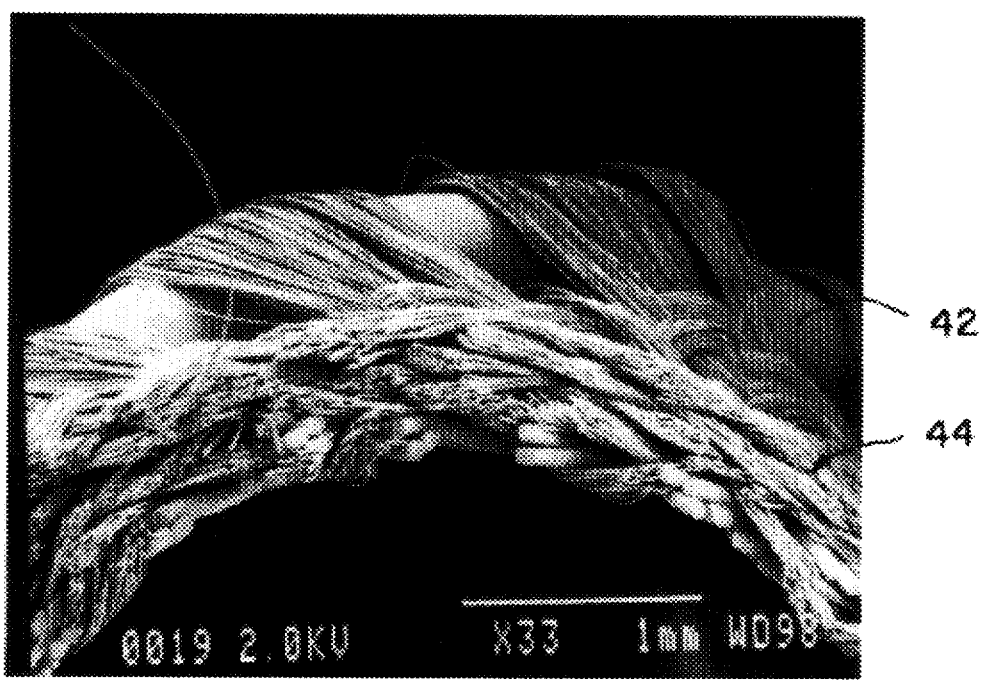
Figure 12:
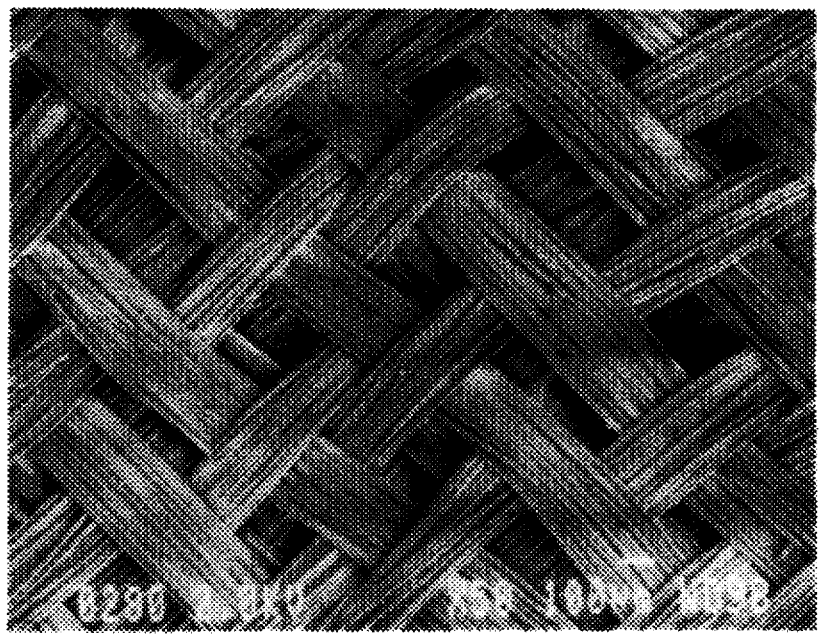
FIGS. 12, 13 and 14 are photomicrographs at X50, X50 and X15 magnification respectively which show the interior and exterior surfaces of a braided prosthesis in accordance with the present invention.
Figure 13:
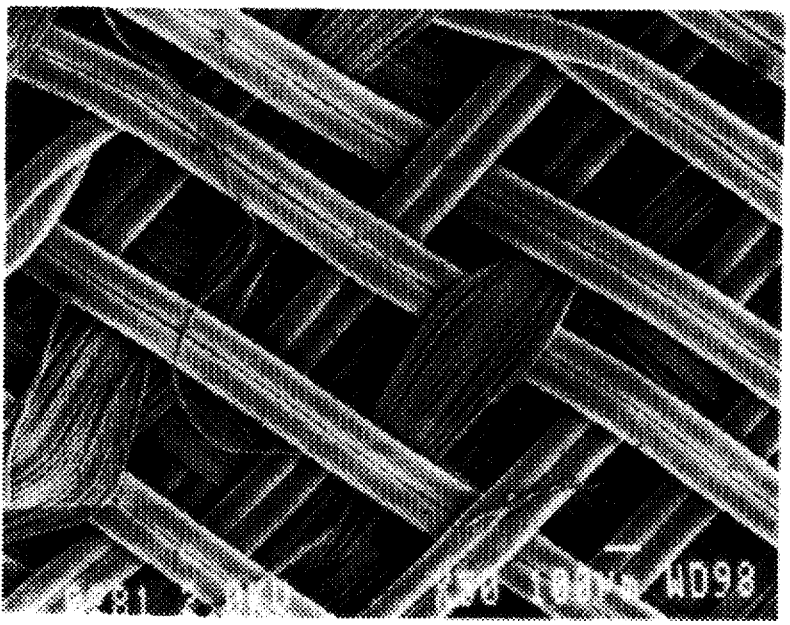
Figure 14:
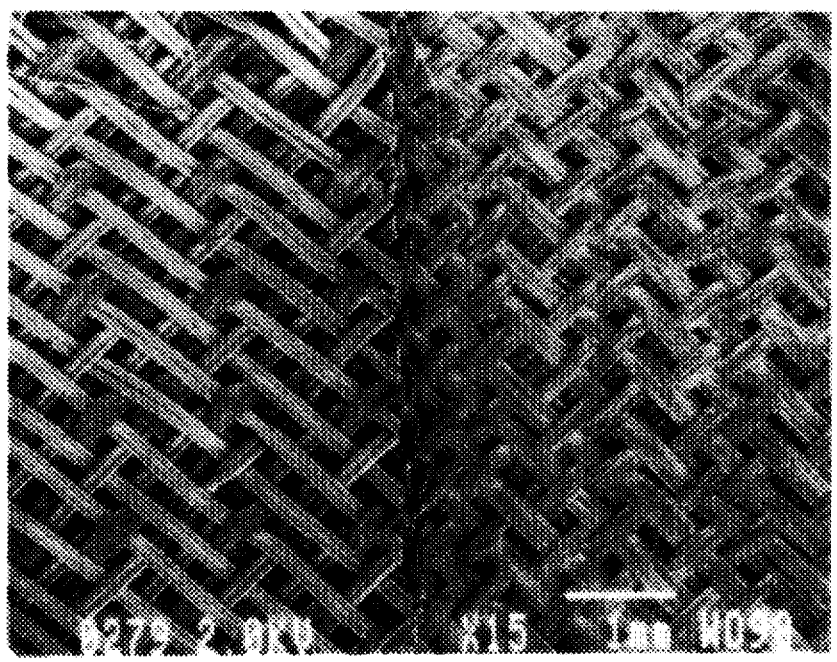
Figure 15A:
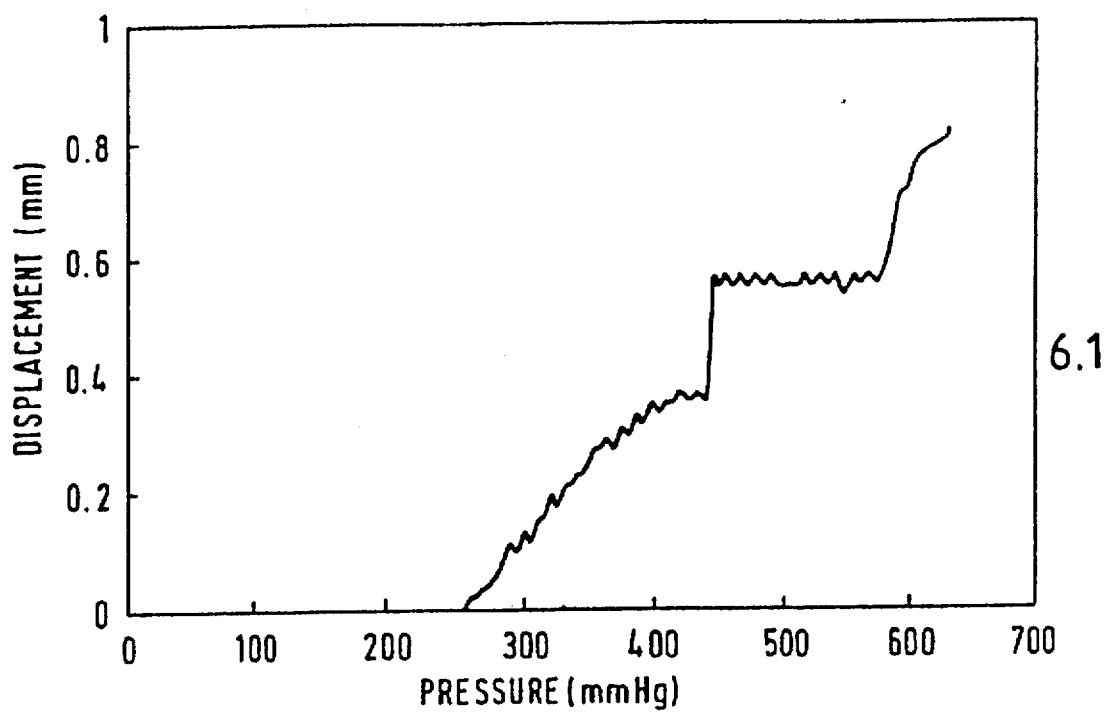
FIG. 15 shows a graph of radial displacement as a function of positive radial pressure for each of six sample prosthesis in accordance with the present invention.
Figure 15B:
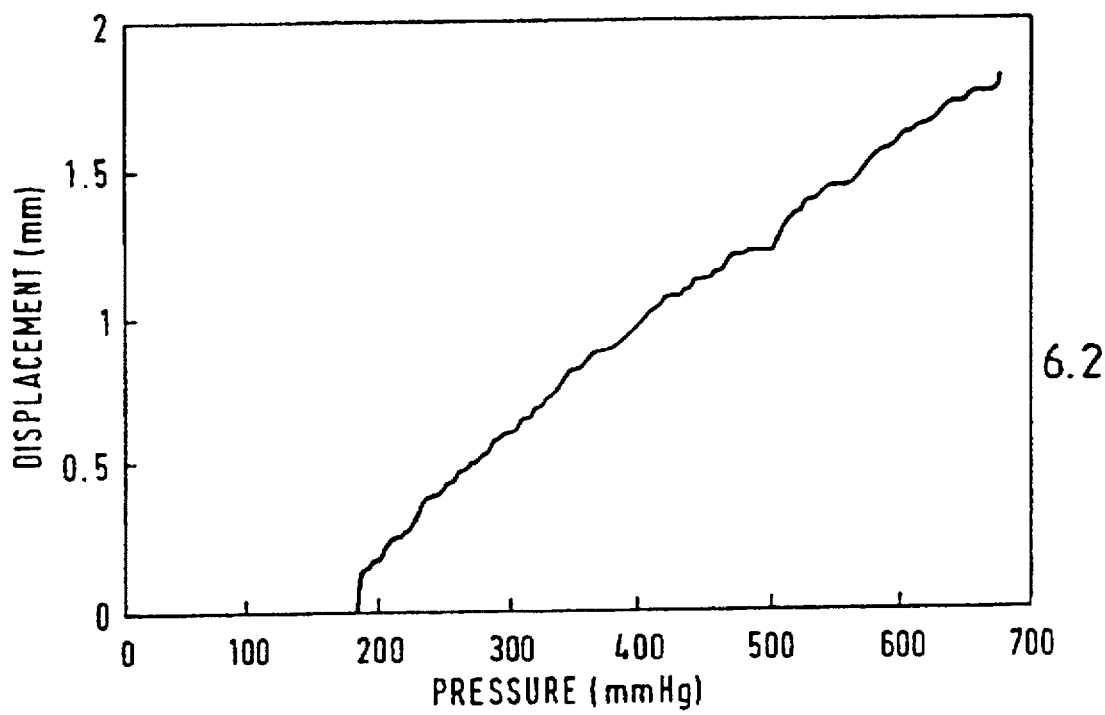
Figure 15C:
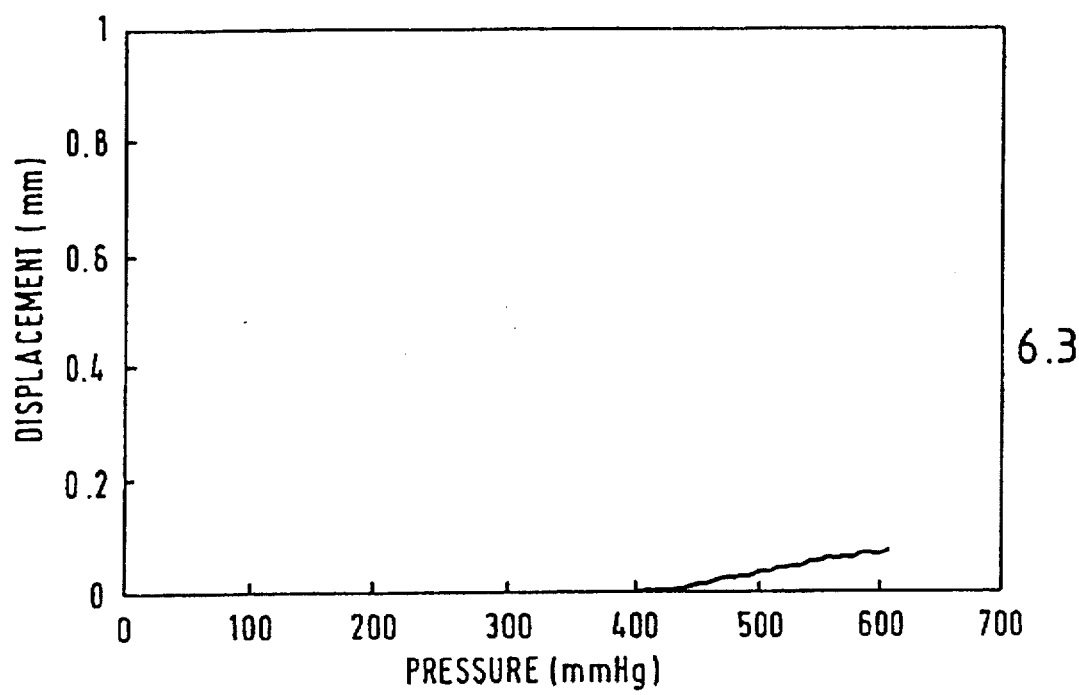
Figure 15D:
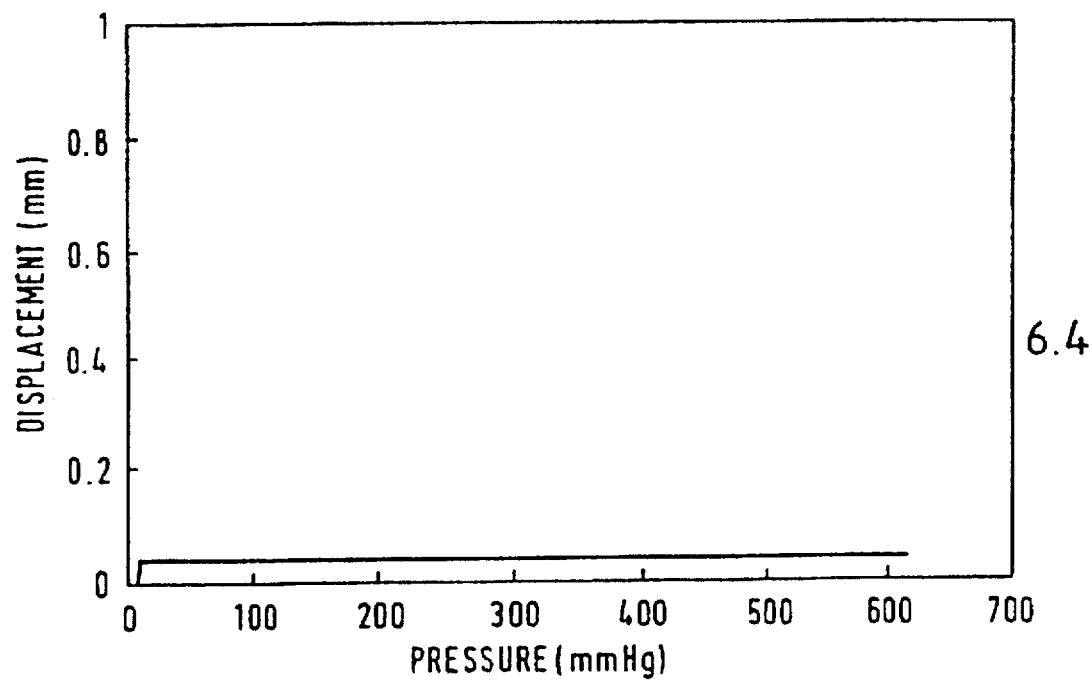
Figure 15E:
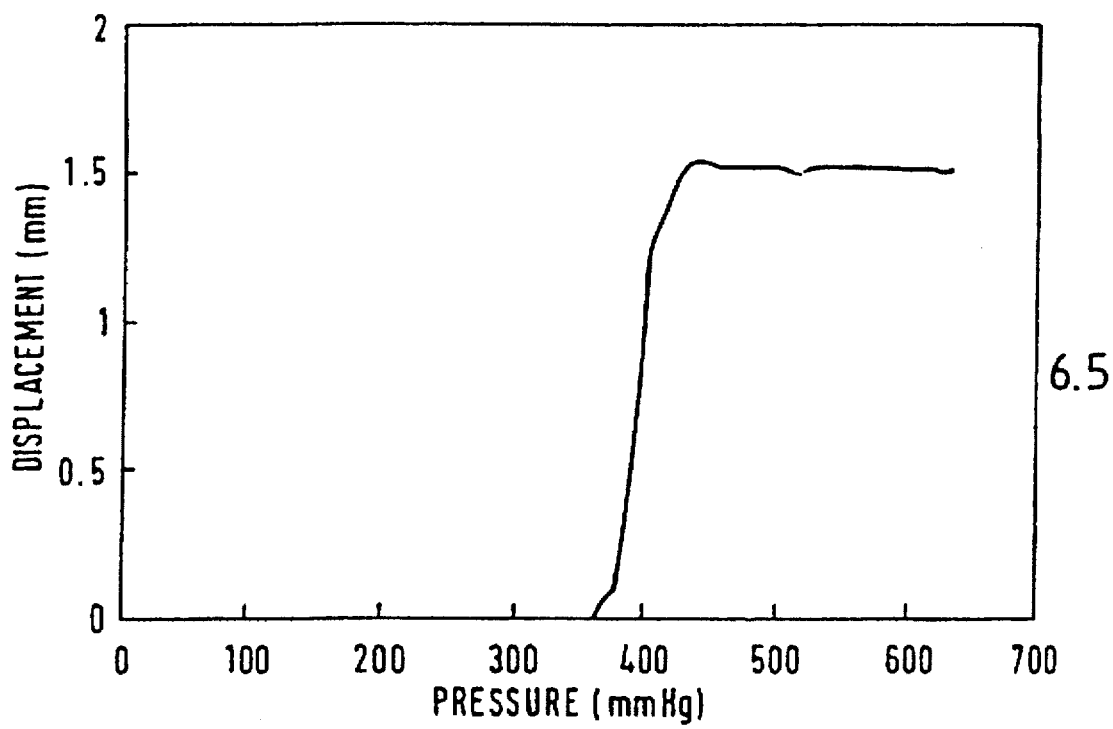
Figure 15F:
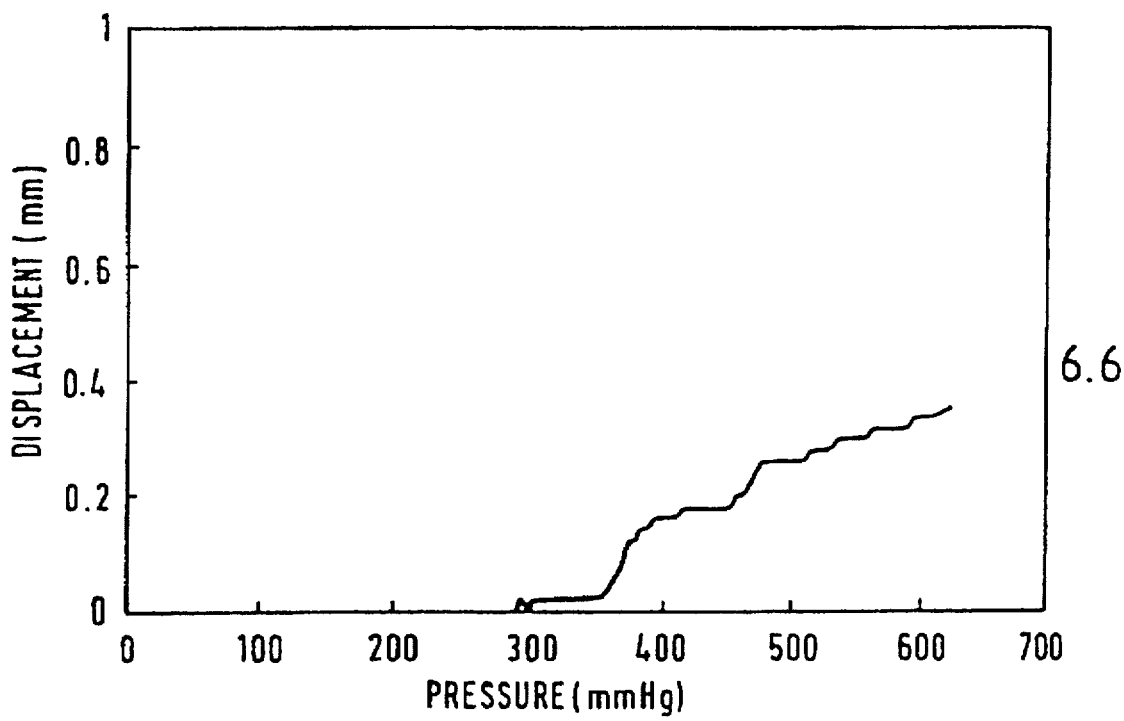

FIGS. 5 to 10 show various photomicrographs of the prosthesis (40). In FIGS. 5, 6, 9 and 10 the photomicrographs show clearly the helical wrap (42) of polyester monofilament which is incorporated into the braid structure of the outer braid layer of the prosthesis (40). Wrap (42) is interbraided with the DACRON polyester multifilament yarns (44) and is not interlocked with yarns in any of the intermediate layers or inner braid layer. In FIGS. 7 and 8, the inner braid layer (46) of prosthesis (40) includes non-absorbable DACRON multi filament polyester yarns (44) which are interbraided with the said resorbable MAXON suture yarns (48).

Figure 11:
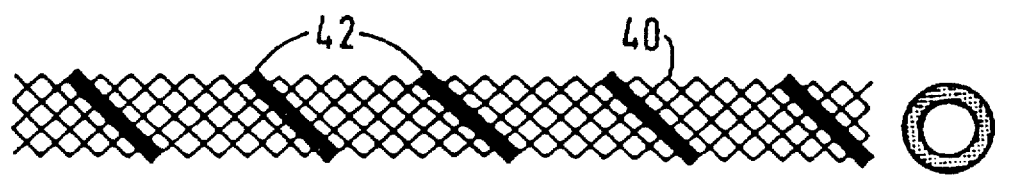
FIG. 11 is a schematic illustration which shows the effect of systole on the prosthesis of FIG. 4.
Figure 11:
Figure 11:
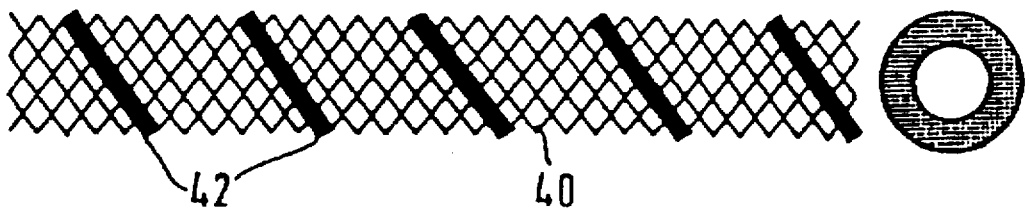
Figure 5A:
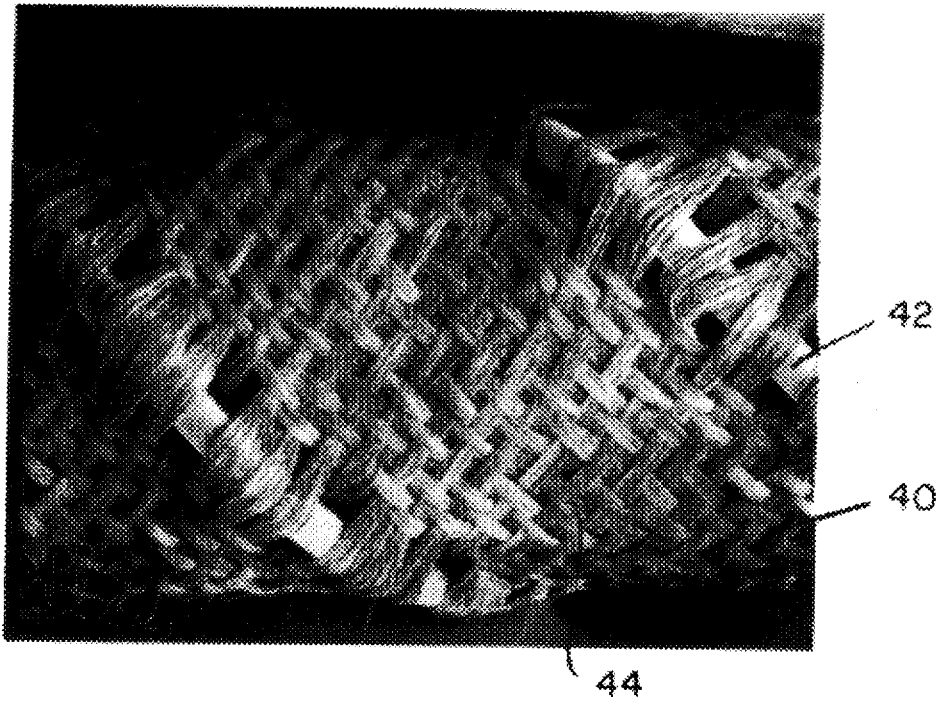
FIG. 5 is two photomicrographs at X11 magnification which show the external surface of the supported tubular braided prosthesis of FIG. 4.
Figure 5B:
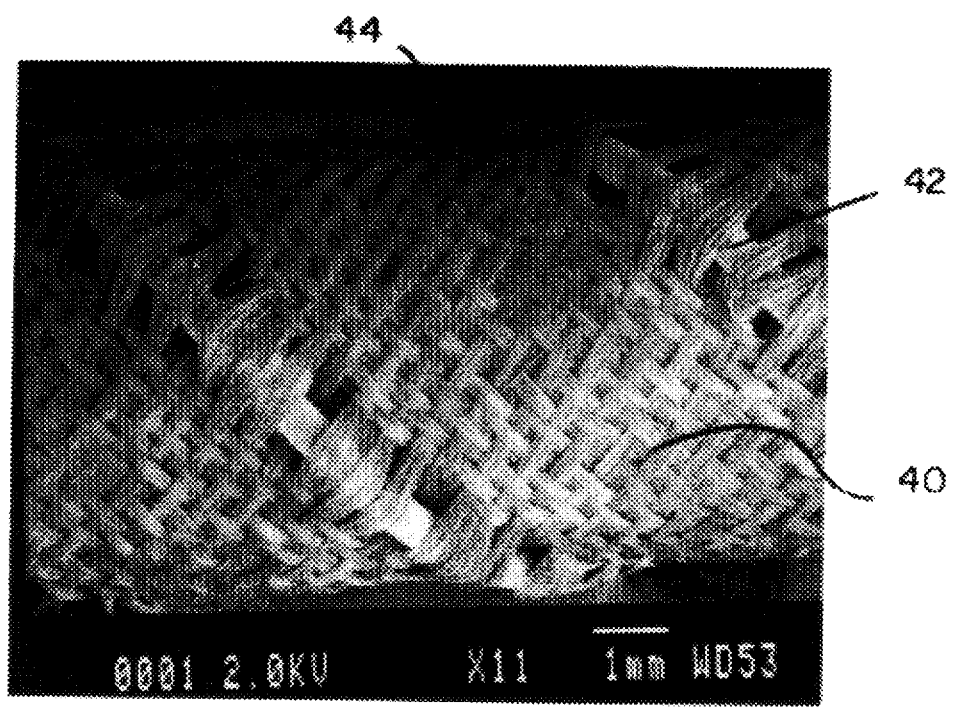

FIG. 11 shows schematically the effect of cardiac systole on the prosthesis (40) which has a stress-strain relationship similar to that shown in FIG. 2 in connection with Example 1 above. It will be appreciated that a tubular braid structure allows reorganisation and relative movement of the interbraided yarns to accommodate or allow changes in diameter of the tubular braid, and the low radial compliance of prosthesis (40) allows the diameter of the prosthesis (40) to expand during systole in a manner which matches closely the systolic response of natural blood vessels.

EXAMPLE 4

A five-layer interbraided tubular prosthesis was made on a 6 mm diameter stainless steel mandrel using a braider having 48 package carriers at a nominal braid orientation angle of 55° to the longitudinal axis of the mandrel. The inner braid layer was formed substantially of 48 resorbable, polylactic acid-based 7/0 USP suture yarns such as those which are commercially available under the Trade Mark MAXON: the next adjacent layer was formed substantially of 24 MAXON 7/0 suture yarns and 24 multifilament polyester yarns of 70 denier commercially available under the Trade Mark DACRON type 56: and the other two intermediate layers and the outer braid layer were each formed substantially of 48 DACRON type 56 yarns of 70 denier. After braiding, the prosthesis was removed from the 6 mm mandrel and placed on a 5 mm diameter mandrel. The prosthesis was then stretched in a longitudinal direction to cause the prosthesis to form a conformate fit to the surface of the smaller mandrel, and the mandrel/prosthesis was placed for 30 minutes in an oven heated to 150° C. After cooling the tubular prosthesis was removed from the mandrel for use.

EXAMPLE 5

A tubular, five-layer braided prosthesis was prepared as described above in Example 4. The inner braid layer was formed substantially of 48 MAXON 7/0 suture yarns, and the four other layers were each formed substantially of 48 DACRON type 56 yarns of 55 denier. FIG. 6 is a photomicrograph of the surface of the outer braid layer having braided non-absorbable yarns (62). FIG. 7 is a photomicrograph of the surface of the inner braid layer which comprises resorbable yarns (72) which are interbraided with yarns (74) of the next adjacent layer diverted into the inner layer to form an interlock therewith.

In FIG. 8, the two surfaces are shown side-by-side for comparison.

EXAMPLE 6

Six tubular prostheses (Examples 6.1 to 6.6) were made as described above under Example 4. Each prosthesis was braided onto a 6 mm diameter mandrel and then transferred to a 4.75 mm mandrel and heat set for 30 minutes at 150° C. In each case, the prosthesis comprised five interbraided braid layers: the inner braid layer was formed from 48 MAXON 5/0 suture yarns (except Example 6.2), and the three intermediate layers were each formed from 48 DACRON type 56 multifilament yarns, each multifilament yarn comprising 34 monofilaments and having a total denier of 70. In the case of Example 6.2, the inner layer was formed of 48 DACRON multifilament yarns. The composition of the outer braid layer of each prosthesis was as follows:

| Prosthesis Number | Composition of Innerbraid Layer |
|---|---|
| 6.1 | 46 DACRON type 56 (70 denier, 34 monofilament) multifilament yarns |
| 6.2 | 48 DACRON type 56 (70 denier, 34 monofilament) multifilament yarns |
| 6.3 | 47 DACRON type 56 (70 denier, 34 monofilament) multifilament yarns and one braided cord comprising 16 DACRON type 56 (70 denier, 34 monofilament) multifilament yarns |
| 6.4 | 46 DACRON type 56 (70 denier, 34 monofilament) multifilament yarns and two braided cords, each cord comprising 16 DACRON type 56 (70 denier, 34 monofilament) multifilament yarns. |
| 6.5 | 46 DACRON type 56 (70 denier, 34 monofilament) multifilament yarns and two 0.012 mil polyester monofilaments |
| 6.6 | 47 DACRON type 56 (70 denier, 34 monofilament) multifilament yarns and one braided cord comprising 16 interbraided DACRON type 56 (70 denier, 34 monofilament) yarns. |

After heat setting, each prosthesis was cooled and removed from the 4.75 mm mandrel. The radial compliance of each prosthesis was then measured by subjecting the prosthesis to internal positive pressure and measuring the radial displacement. The results of such tests are shown in FIG. 15 (a) to (f) each of which shows a graph of displacement in millimeters against the outwardly directed radial pressure in mmHg for each of the six prostheses 6.1 to 6.6 respectively. In each case, the prosthesis was held under a 400 g axial load, and the following table shows the threshold pressure for each prosthesis for the onset of radial displacement.

TABLE 1

| Prosthesis Number | Onset of radial displacement/psi |
|---|---|
| 6.1 | 250 |
| 6.2 | 180 |
| 6.3 | 410 |
| 6.4 | No significant radial displacement reached |
| 6.5 | 360 |
| 6.6 | 300 |

When a typical tubular prosthesis in accordance with the present invention is first implanted in a patient, the structure of the prosthesis provides intrinsic support; the braided prosthesis provides a graft which is initially impermeable to blood in pre-heparinized patients, but, as time progresses, the biologically resorbable material that forms the inner surface layer and parts of intermediate layers is resorbed, and body tissue is allowed to grow into interstices which are formed in the residual braided structure of non-resorbable yarns, which structure provides a geometrically stable support.

It has been found that the stress-strain relationship of a prosthesis according to the present invention typically exhibits a low radial compliance and a high compression resistance which allows the prosthesis to mimic closely the properties of natural blood vessels. Further, the use of braiding technology as described in the applicant's WO91/10766 allows the provision of a tubular vascular prosthesis having a diameter of 6 mm or less which is less liable to kinking and aneurysm as compared with known grafts.

We claim:

1. A prosthetic device, comprising:
    an implantable three-dimensional braided tubular structure having a plurality of braided layers including an inner surface substantially formed of resorbable yarn and an outer surface substantially formed of non-absorbable yarn wherein each layer includes at least one interlocking yarn which extends into another layer to form an interlock therewith whereby said device maintains its structural integrity as said resorbable yarn is resorbed.

2. The prosthetic device according to claim 1, wherein said resorbable material comprises biologically resorbable yarns.

3. The prosthetic device according to claim 2, wherein said yarns are selected from the group consisting of catgut, reconstituted collagen, polyglycolic acid, polydioxanone and poly(glycolide-trimethylene carbonate).

4. The prosthetic device according to claim 1, wherein said structure further includes at least one intermediate layer between said surface layers.

5. The prosthetic device according to claim 1, further comprising non-absorbable external support means surrounding said structure.

6. The prosthetic device according to claim 5, wherein said support means includes at least one wrap forming a helical path around the exterior of said structure.

7. The prosthetic device according to claim 6, wherein said wrap is formed of an elongate textile structure having a substantially high bending modulus.

8. The prosthetic device according to claim 6, wherein said wrap is formed of monofilament yarns having a substantially high denier.

9. The prosthetic device according to claim 6, wherein said wrap is formed of multifilament yarns having a composite denier and linear density greater than that of said braided structure.

10. The prosthetic device according to claim 6, wherein said wrap is externally attached to said structure by an adhesive.

11. The prosthetic device according to claim 6, wherein said wrap is incorporated into a layer of said braided structure.

12. The prosthetic device according to claim 11, wherein said wrap is incorporated into an outer surface layer of said structure and forms a helical path therein.

13. The prosthetic device according to claim 6, wherein said wrap is formed of a non-absorbable material.

14. The prosthetic device according to claim 5, wherein said support means includes first and second wraps forming helical paths around the exterior of said structure, said first wrap forming a helical path opposite to that of said second wrap.

15. A method of repairing a tubular vessel in a patient's body, comprising:
    removing a damaged portion of said tubular vessel from said patient's body;
    braiding a three-dimensional braided interlocking structure on a mandrel having an outside diameter corresponding to the inside diameter of said tubular vessel to provide a prosthesis, said structure having a plurality of braided layers formed of resorbable and non-absorbable yarn wherein each layer includes at least one interlocking yarn which extends into another layer to form an interlock therewith whereby said device maintains its structural integrity as said resorbable yarn is resorbed;

positioning said prosthesis into the region of said vessel from which said damaged portion was removed; and securing each end of said prosthesis to a respective end of said vessel whereby a continuous fluid pathway is re-established along said vessel.

* * * * *

UNITED STATES PATENT AND TRADEMARK OFFICE
CERTIFICATE OF CORRECTION

PATENT NO. : 5,697,969
DATED : December 16, 1997
INVENTOR(S) : Peter J. Schmitt, David Stuart Brookstein and John Skelton It is certified that error appears in the above-indentified patent and that said Letters Patent is hereby corrected as shown below:

| | |
|---|---|
| At Column 1, line 38, | "when the dieter of the" should be --when the diameter of the--; |
| At Column 2, line 26, | "my also" should be --may also--; |
| At Column 2, line 61, | "wrap(s) my be" should be --wrap(s) may be--; |
| At Column 5, line 3, | "pans (11A)" should be --parts (11A)--; |
| At Column 5, line 37, | "0.012" dieter" should be --0.012" diameter--; |
| At Column 6, line 63, | "multifilament yams," should be --multifilament yarns,--; |
| At Column 7, line 4, | "46 DACRON type 56" should be --48 DACRON type 56--; |

Signed and Sealed this

Twenty-eighth Day of July, 1998

Attest:

BRUCE LEHMAN

Attesting Officer        Commissioner of Patents and Trademarks